United States Patent [19]
Fix, Sr. et al.

[11] Patent Number: 6,111,238
[45] Date of Patent: Aug. 29, 2000

[54] AUTOMATED FOCUSED MICROWAVE SAMPLE DIGESTION SYSTEM

[75] Inventors: Robert Joseph Fix, Sr., Kernersville; Jannell Mills Rowe, Clemmons; Samuel Mark DeBusk, Lexington; Bain Clifford McConnell, Clemmons; John Larkin Nelson, Lewisville; Nancy Carol Huettel, Pfafftown, all of N.C.

[73] Assignee: R. J. Reynolds Tobacco Company, Winston-Salem, N.C.

[21] Appl. No.: 09/034,454

[22] Filed: Mar. 4, 1998

[51] Int. Cl.[7] .............................. H05B 6/68; H05B 6/78
[52] U.S. Cl. ........................ 219/700; 219/702; 422/21; 414/222
[58] Field of Search ...................... 219/700, 701, 219/702, 388; 422/21, 114, 105, 186; 414/467, 222, 273

[56] References Cited

U.S. PATENT DOCUMENTS

| | | | |
|---|---|---|---|
| 4,687,895 | 8/1987 | Chitre et al. | 219/701 |
| 5,096,670 | 3/1992 | Harris et al. | 422/65 |
| 5,111,855 | 5/1992 | Boeck et al. | 141/83 |
| 5,132,504 | 7/1992 | Iijima | 219/700 |
| 5,436,432 | 7/1995 | Cyr | 219/700 |
| 5,792,421 | 8/1998 | Riley | 219/679 |

OTHER PUBLICATIONS

Operation Manual, STAR System 2™ and STAR System 6™, CEM Corporation, Aug. 1996, pp. i–iii and 1–42.
Microdigest™ 301 & A301, "Focused Microwaves" Groupe Phone–Poulenc, Booklet.
Microwave Digester Manual 301, Instruction for use, Groupe Rhone–Poulenc, Booklet, pp. 1–49.

*Primary Examiner*—Philip H. Leung

[57] ABSTRACT

An automated microwave sample digestion system is disclosed in which a focused microwave digestion system is operated under computer control in association with a computer controlled robotic positioning system such that sample tubes containing samples to be digested are loaded and unloaded into and out from the cooking cavities of the microwave digestion oven in a preprogrammed manner in order to both increase the efficiency of the processing of samples as well as to produce consistent operating conditions for each sample being digested. An additional pump and syringe line is provided for both washing the tube condenser utilized during the digestion process as well as for diluting the digested sample.

17 Claims, 5 Drawing Sheets

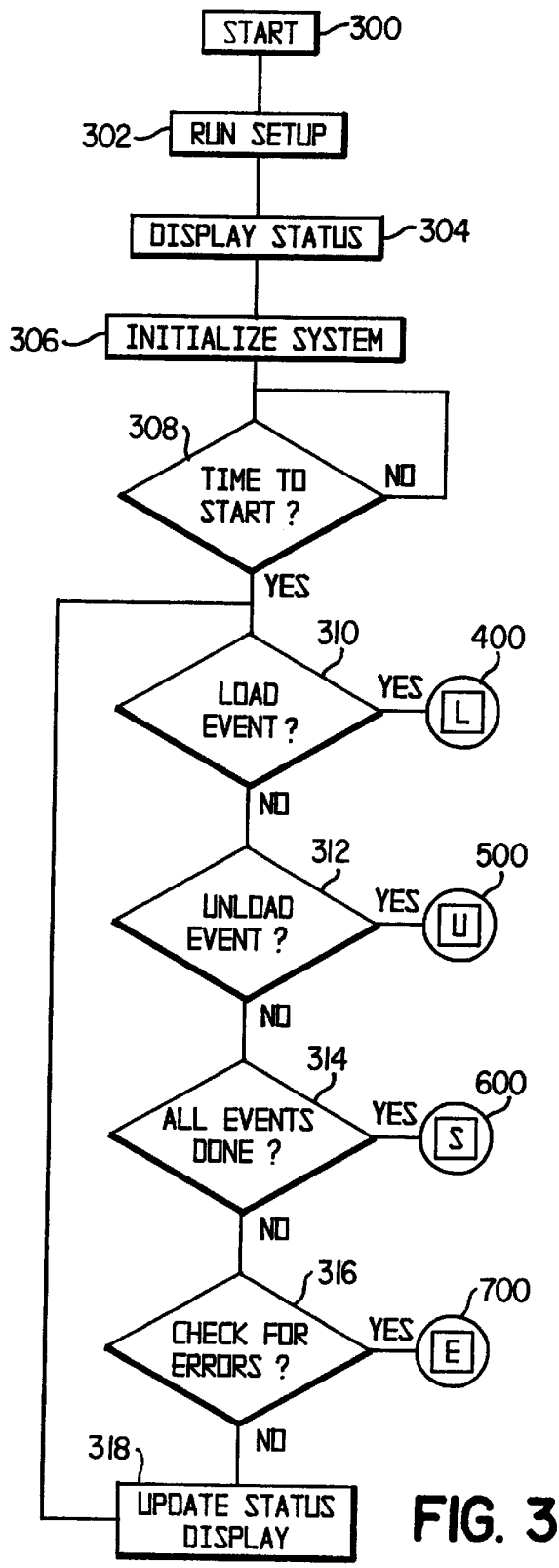
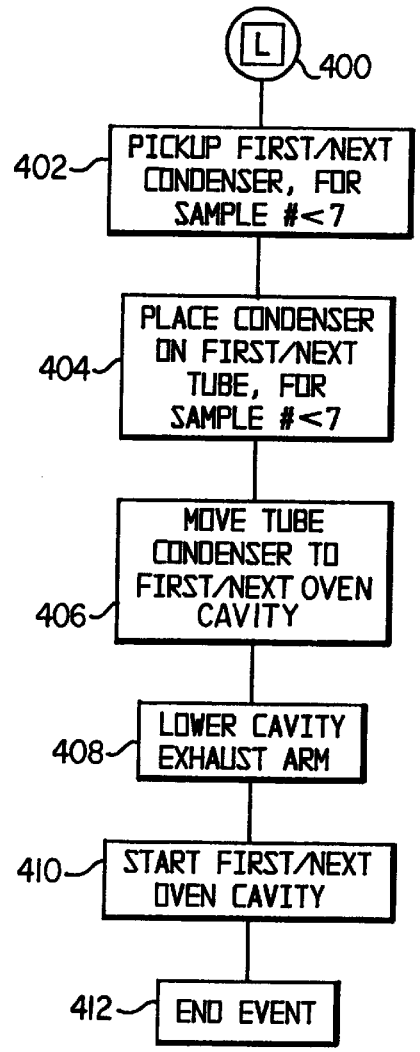
FIG. 3
FIG. 4

AUTOMATED FOCUSED MICROWAVE SAMPLE DIGESTION SYSTEM

BACKGROUND OF THE INVENTION

The present invention is directed to a method of and apparatus for operating a focused microwave sample digestion system such that, once set up, human intervention is not required. More particularly, the present invention is directed to a method of and apparatus for automatically operating a focused microwave sample digestion system in which a plurality of prepared samples are moved through a focused microwave digestion system and then placed in a storage rack after each of the samples has been processed, all in an automatic manner, without the need for human intervention.

During the process of testing for the presence of trace metals in certain organic samples, such as tobacco or paper samples, it is necessary to destroy all of the organic material contained in the sample. Such destruction is typically performed by adding an acid, such as concentrated nitric acid, to a vessel containing the sample and then cooking or digesting the sample at a very high temperature.

Typically, the sample and nitric acid combination is digested in a microwave oven, in order to prepare the sample for trace analysis by an inductively coupled plasma optical emission instrument. Recently, however, focused microwave-based systems have become available which allow speeded-up digestion times. One such microwave digestion oven is the CEM STAR 6 Focused Microwave System, which is available from CEM, Inc., of Matthews, N.C. Using the STAR 6 Focused Microwave System, it is possible to digest a sample in approximately 15 minutes, with six samples being digested at one time. Thus, for example, in order to digest 24 samples, one hour is required. Additional time is necessary, however, to load and unload the samples. Using prior microwave technology, it takes about 4.5 to 5.0 hours to digest 24 samples.

However, even though using the STAR 6 Focused Microwave System speeds up the cooking process, it still requires the full attention of a lab analyst who must load the sample tubes into the microwave oven system, start the microwave oven system, and monitor the system while it is digesting samples. It would, however, be advantageous to perform the digestion process and loading and unloading operations on an automated basis such that lab personnel would be freed up for performing other tasks. In addition, if the digesting process were automated, it could be operated unattended after business hours, which would likewise serve to increase the sample capacity throughput. That would allow the laboratory utilizing the automated system to keep pace with increased testing demands. In addition, more uniform results could be obtained if the steps involved in performing the acid digestion were uniformly applied under computer control, rather than being performed on an as-needed basis by a laboratory technician.

SUMMARY AND OBJECTS OF THE INVENTION

In light of the shortcomings of the prior art microwave digesting ovens and particularly with respect to the efficiency and throughput which can now be attained with focused microwave digestion ovens, it is clear that there exists a need in the art for an automated focused microwave sample digestion system which can be used to automatically control and feed samples for digestion to a microwave digestion oven in such a manner that the samples can be run through the digestion process without the need for human intervention. It is, therefore, a primary object of the present invention to provide a system for operating a microwave digestion oven to process a plurality of samples, all without the need for human intervention.

It is also a primary object of the present invention to provide an automated microwave digestion oven system for digesting samples which is able to accurately and repeatedly reproduce the same processing of a series of the same sample in a simple, accurate and reliable manner and without human intervention.

It is a further object of the present invention to provide an automated microwave digestion oven system which can be operated so as to maximize the throughput of digesting samples through the microwave oven so that a maximum number of samples can be processed within a 24 hour period.

These and other objects of the present invention are accomplished by providing a robotic positioning system and a microwave digestion oven, together with a supervisory computer which operates both the microwave digestion oven and the robotic positioning system. Under computer control, the robotic positioning system loads and unloads the sample tubes containing the samples to be digested into the individual cavities of the microwave digestion oven. In addition, the gripper jaws of the robotic gantry are used to place the tube condenser on each sample tube prior to the digestion process and to remove the tube condenser from each sample tube after the digestion process. The robotic gantry also moves the reagent/exhaust arm of the microwave digestion oven into and out of its operating position. It further serves to cap the sample tubes.

The microwave digestion oven is operated under supervisory control of a computer to control the temperature and time for the digestion process, as well as for adding acid and other reagents used in the digestive process, as necessary. An additional syringe line is provided for washing the tube condenser and for diluting the sample after it has been digested.

BRIEF DESCRIPTION OF THE DRAWINGS

FIG. 3 is a flow chart diagram showing the overall control steps of the software which operates the apparatus of the present invention;

FIG. 4 is a flow chart diagram of the load event subroutine of the software which operates the apparatus of the present invention;

DETAILED DESCRIPTION OF THE PREFERRED EMBODIMENT

Figure 1:
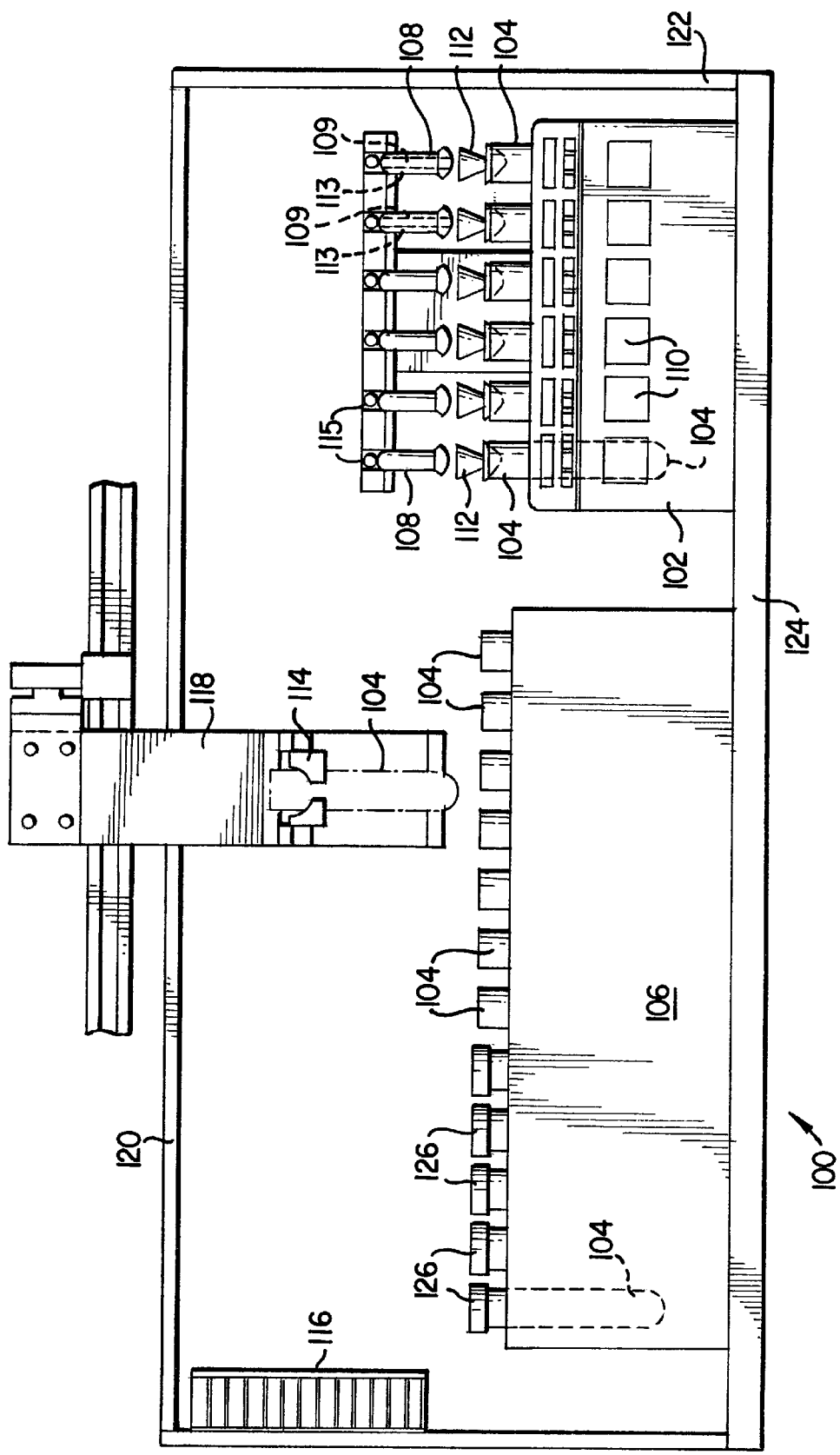
FIG. 1 is a perspective drawing showing the microwave digestion oven, sample tubes and rack and gantry support and movement system of the present invention.

Referring now to the drawings wherein like parts are designated by like references numerals throughout, there is shown in FIG. 1 a diagrammatic drawing of the microwave digestion system of the present invention. The automated microwave digestion system of the present invention utilizes a CEM STAR 6 focused microwave oven. By utilizing such a microwave oven for the digestion process, together with the automated system as described herein, 18 to 24 samples can be prepared in one hour. Formerly, digesting 24 samples manually took about 4.5 hours.

As shown in FIG. 1, the microwave digestion oven 102 is placed on a table or other working surface 124. X and y direction gantry supports 120 and 122 are constructed to surround the working surface 124. Such gantry supports 120 and 122 as well as the z gantry 118 and the controls therefor are available from, for example, IAI America, Inc., of Torrance, Calif. and other manufacturers of robotic positioning systems. Since such robotic positioning systems are well known in the art, it is not believed necessary to further describe the details of the robotic positioning system used with the present invention.

The microwave oven 102 includes six digestion system cells 110. The microwave oven 102 also includes a like plurality of reagent/exhaust arms 108. An on-board syringe in the microwave oven 102 is connected on its input side, through a series of electronically controlled valves, to up to four different reagent lines. Those reagent lines made in turn be connected to feed up to four difference reagents. On its output side, the on-board syringe is connected to a reagent syringe line 109, which is located inside of each of the hollow reagent/exhaust arms 108. In addition, an auxiliary syringe pump 204, such as that available from the Kloehn Company of Las Vegas, Nev., is connected on its output side to each of six syringe lines 113, each of which is likewise routed through the reagent/exhaust arm 108 (only two are shown). The input of the syringe pump 204 is connected to a source of de-ionized water which is used for washing each of the six condensers 112 which are placed on top of each of the sample tubes 104 to prevent cross-contamination between samples prior to moving the tube condenser 112 to a new sample tube 104 after digestion of the sample in the current sample tube has been completed. The de-ionized water added to the sample tube by means of the syringe 204 and syringe line 113 is also used to dilute the digested sample. It is also used for cleaning the syringe lines 113.

During the digestion process, nitric acid is added to each sample tube 104, both immediately prior to beginning the digestion process and as necessary, using the reagent syringe line 109 contained in each reagent/exhaust arm 108. Other reagents may obviously be added in connection with different digesting protocols using the microwave digestion oven 102. Four reagent lines (not shown) under valve control (not shown) are used to feed the microwave digestion oven 102. In the present system, two of those four reagent lines are used to deliver nitric acid and peroxide to the reagent/exhaust arms 108.

A digestion or sample tube rack 106 is placed proximal to the microwave digestion oven 102 on the working surface 124. The digestion tube rack is designed to hold 60 tubes and is preferably mutually fixtured with the microwave digestion oven 102. However, the digestion tube rack 106 can be designed to hold as many tubes as is desired. In addition, a tube condenser rack (not shown) can also be provided in which to store tube condensers 112 when they are not in use.

Each of the digestion tubes 104 may be covered with a stopper 126 while it is sitting in the digestion tube rack 106. The purpose of the stopper 126 is to act as both a dust cover and a tube stopper to ensure the integrity of the sample contained in the digestion tube 104, after digestion. The stopper 126 preferably has a loose fit, which makes it easy to insert by robotic means. The cap station 116 is preferably designed to hold a number of stoppers 126. After a sample has been digested and the digestion tube 104 is returned to the digestion tube rack 106 from the microwave digestion oven 102, a new stopper 126 may be placed onto the tube 104. The cap station 116 is preferably placed in a position convenient to the digestion tube rack 106 such that the gantry 118/tube gripper unit 114 can readily access the caps 126 stored therein.

As also shown in FIG. 1, the gantry 118 to which the tube gripper 114 is connected moves along the xyz axis in a known maimer. The gripper 114 is moved by means of the gantry 118 such that it can reach each of the tubes 104 and move them, as appropriate, into any one of the six microwave cavities or cells 110 of the microwave digestion oven 102, as well as to any workstation positioned to one side of the digestion tube rack 106 or within the work area defined by the x and y gantry supports 120 and 122. The gripper 114 is constructed such that it can be lowered by means of the gantry 118 over the top of a digestion tube 104 and then closed around the digestion tube 104. In addition, the gripper 114 is able to remove the tube condensers 112 from each of the digestion tubes 104.

As briefly described above, each of the digestion tubes 104, after being placed in its respective microwave digestion cell 110 and prior to the digestion process, has a tube condenser placed thereon. A Teflon7 sleeve (not shown) is placed on the bottom portion of each to the tube condensers in order to ease the separation and removal of the tube condenser 112 from the sample tube 104. Each of the tube condensers 112 must be washed between samples in order to prevent cross-contamination. The washing of the tube condensers is accomplished by means of the syringe pump 204 and the syringe lines 113, which pumps deionized water to the spring-loaded reagent/exhaust arm 108 that washes the tube condenser 112 while at the same time making up the standard volume contained in the digestion tube 104 of the digested sample to approximately 100 mLs. Each of the tube condensers 112 is rinsed with de-ionized water after each sample has been digested. It is not necessary that the tube condenser 112 be dried.

The microwave digestion oven 102 includes six reagent/ exhaust arms 108 which are located above each of the microwave digestion cells 110. The gantry 118/gripper 114 combination is used to raise and lower those reagent/exhaust arms 108, as will be described further herein. When moving each reagent/exhaust arm 108 to its lowered position, the gantry 118/gripper 114 combination helps to ensure a tight seal between the reagent/exhaust arm 108 and the tube condenser 112 in order to prevent the escape of acid fumes from the digestion tube 104 during the sample digestion process.

Figure 2:
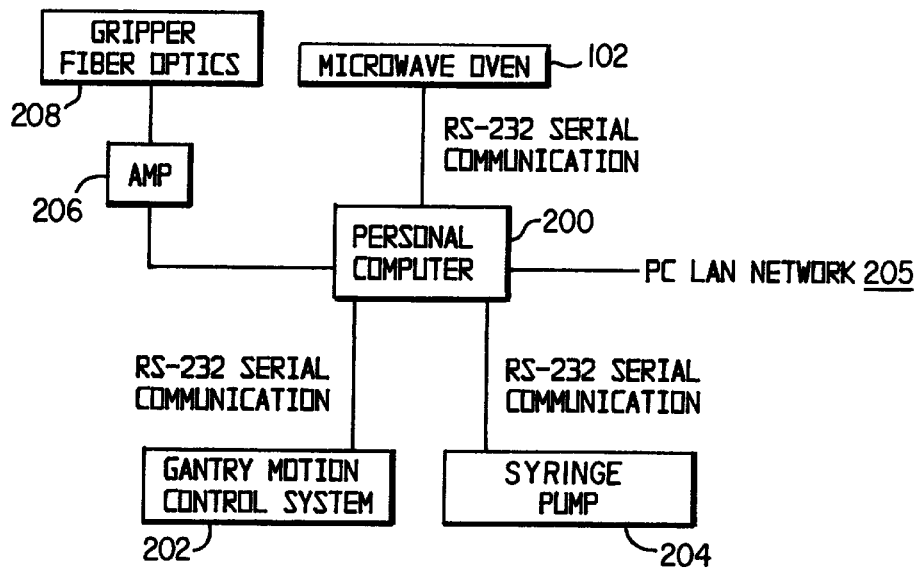
FIG. 2 is a schematic block diagram showing the major system components of the apparatus of the present invention and their communication system.
Figure 9:
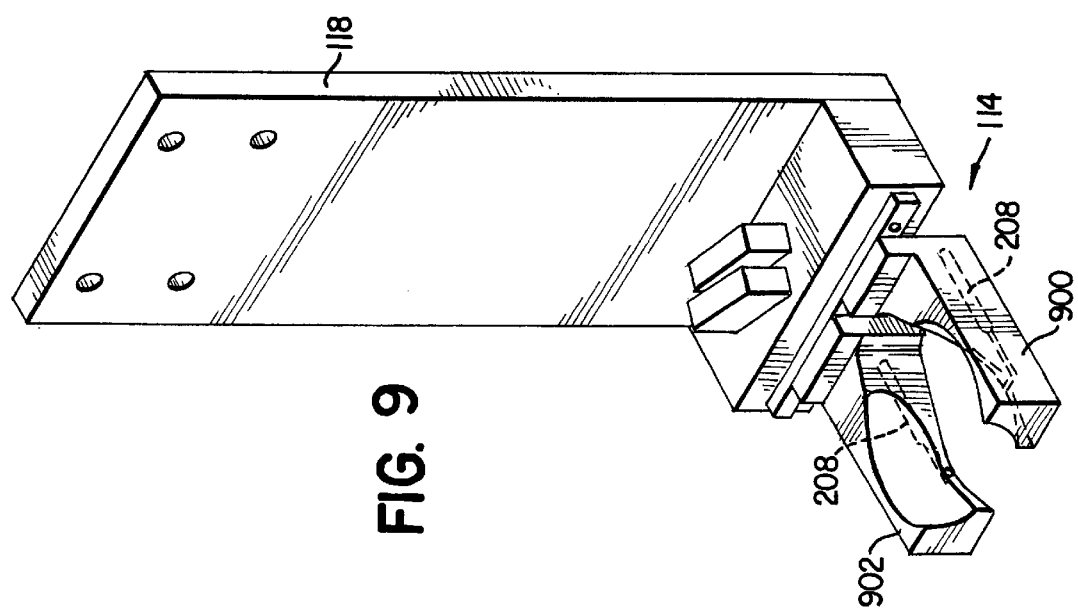
FIG. 9 is a perspective drawing showing the details of the tube gripper used with the gantry of the present invention.

Turning now to FIG. 2, there is shown in schematic block diagram form the major components of the automated microwave digestion system of the present invention. The center of the automated microwave digestion system is the microwave digestion oven 102, which is connected by means of an RS-232 serial connection port and cable to a personal computer 200, which is preferably of the Pentium class. The computer 200 is optionally connected to a PC LAN network 205, for remote communication purposes. The personal computer 200 is also connected, again by means of RS-232 serial ports, to both the gantry motion control system 202 (which is also available from IAI America, Inc.) and to the syringe pump 204. The operation of the automated microwave digestion system, and particularly the software for operating that system, will be described later herein. As shown in FIG. 9, the tube gripper 114 is formed by right and left movable gripper jaws 900 and 902, respectively. For sensing purposes, a Model FU-32 fiber optic sensor 208, available from Keyance Corporation of America, Charlotte, N.C., is embedded in the gripper jaws 900 and 902. The optical fibers 208 are opposed across the area to be occupied by the gripped item, such as the sample tube 104, the tube condenser 112 or the cap 126. When the gripper jaws 900, 902 are closed about an item being gripped, the sensor 208 will be located just below the top rim of the sample tube 104 or just above the male tapered fitting of the tube condenser 112. That geometry allows the detection of multiple conditions of gripped items.

As shown in FIG. 2, the fiber optic sensor 208 is connected to an amplifier 206 and produces two binary outputs which are then fed to the personal computer 200. Each of the two outputs is set to a different threshold of light crossing the gripper jaws 900, 902. Thus, the detection of three distinct states is provided for.

The first state to be detected occurs when the maximum light transmission across the gripper jaws 900, 902 is detected. That indicates that nothing is captured within the gripper jaws 114. In this state, both outputs from the amplifier 206 are true. This first state is used to ensure that a sample tube 104 or tube condenser 112 has in fact been released at the desired time or to verify that a sample tube 104 is not present as expected (for example, to verify an empty position in the microwave digestion oven 102).

The second state, in which one output of the amplifier 206 is on and the other output is off, is utilized to detect a condition in which only a sample tube 104 is being gripped by the tube gripper 114, and that no tube condenser 112 or cap 126 is present. That state allows verification that a sample tube 104 has been moved and that there is no tube condenser 112 or cap 126 present and thus the system is clear to insert a tube condenser 112 or cap 126 into the sample tube 104.

In the third state, both outputs are off, thus signifying a maximum light attenuation condition. That state is used to detect a sample tube 104 in which either a tube condenser 112 or a cap 126 has been inserted. This third state is used to confirm the insertion of a tube condenser 112 or a cap 126 into a sample tube 104. It is also used to detect the opaque grappling fixture 115 located on top of each of the reagent/exhaust arms 108 of the microwave digestion oven 102.

As will be described further herein, the gripper jaws 900, 902 are used to lift and transport the sample and tube condensers 104 and 112. The gripper 114 also serves to separate each tube condenser 112 from each sample tube 104, as necessary. The gripper 114 performs the function of separating the tube condenser 112 from the sample tube 104 by wedging the bottom portion of each of the gripper jaws 900, 902 in between the bottom or radius portion of the tube condenser 112 and the top of the sample tube 104.

As also discussed above, the gripper 114 is used to transport the sample tubes 104 between the digestion tube rack 106 and the microwave digestion oven 102. It is also used to transport the tube condensers 112 between the microwave digestion oven 102 and the tube condenser rack, as well as between successive sample tubes 104. During the transportation of the sample and tube condensers 104 and 112, those pieces are held in the gripper jaws 900, 902 so that they do not move. The gripper jaws 900, 902 are also used to lift and lower the reagent/exhaust arms 108 which form part of the microwave digestion oven 102. An opaque grappling fixture or disc 115 mounted on each of the reagent/exhaust arms 108 has a radius that closely matches the radius of the gripper jaws 900, 902, such that the gripper 114 and the grappling fixture 115 act like a ball and socket joint.

Figure 8:
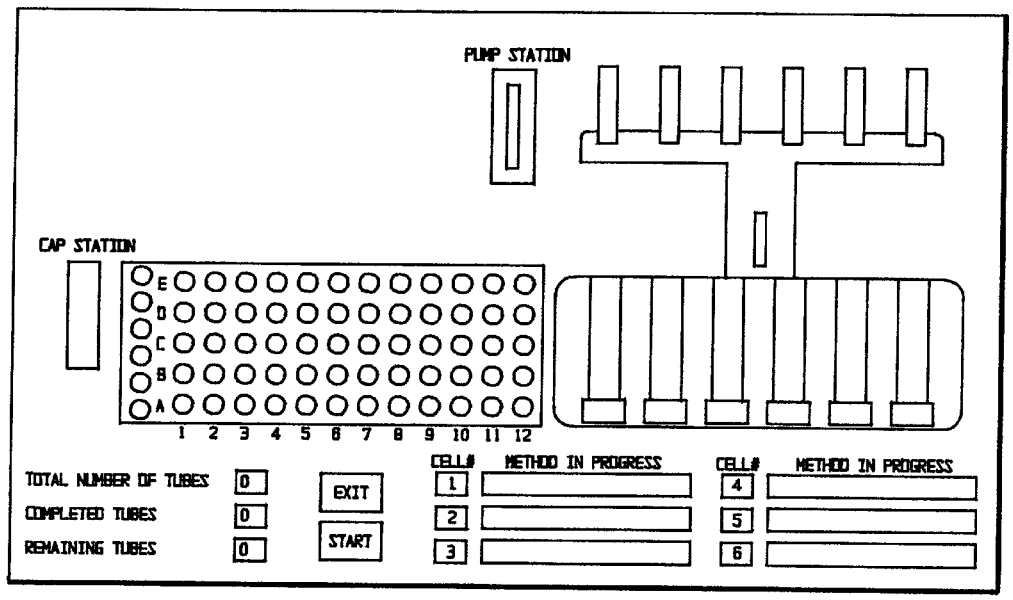
FIG. 8 is a drawing of a control screen used by the operator of the present invention to control and monitor the status of the automated sample digestion system and process of the present invention.
Figure 5:
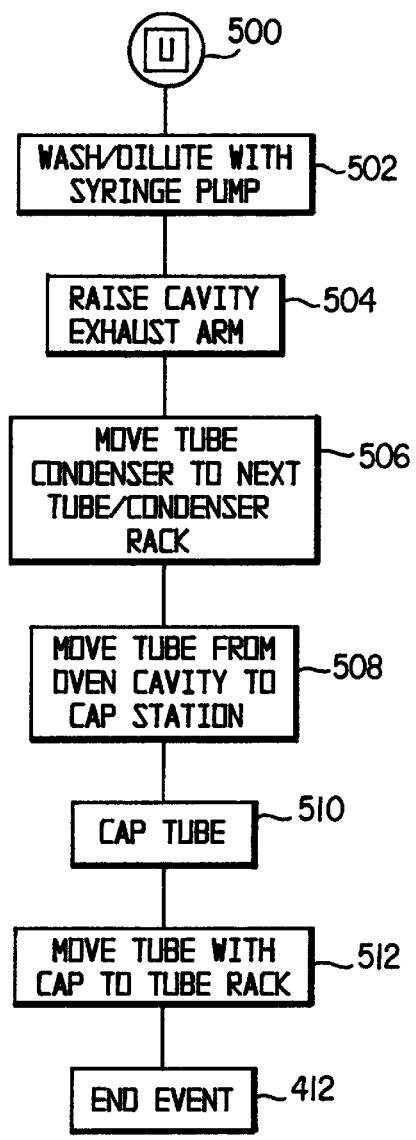
FIG. 5 is a flow chart diagram of the unload event subroutine of the software which operates the apparatus of the present invention.
Figure 6:
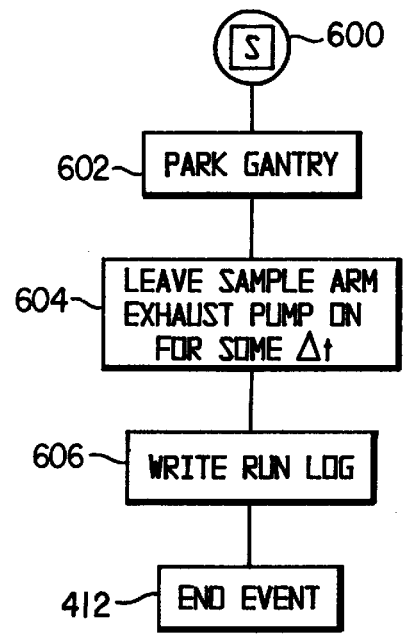
FIG. 6 is a flow chart diagram of the shutdown event subroutine of the software which operates the apparatus of the present invention.
Figure 7:
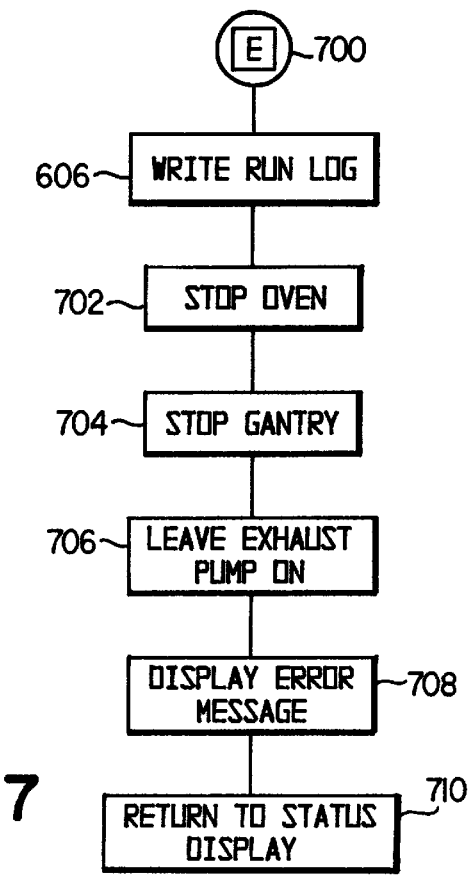
FIG. 7 is a flow chart diagram of the error event subroutine of the software which operates the apparatus of the present invention.

Turning now to FIGS. 3 through 7, there is shown, in diagrammatic flowchart form, the supervisory software (FIG. 3) for operating the automated microwave digestion system of the present invention and each of the subroutines for performing certain functions of the automated digestion microwave system of the present invention, at a somewhat lower level (FIGS. 4–7). When the system of the present invention is first turned on, it starts at 300 and then runs the setup subroutines at step 302. Then, at 304, a display status is shown on the monitor of the personal computer 200 (it should be understood that the element 200 shown in FIG. 2 is intended to include all of the requisite components of a personal computer, including, without limitation, monitor, network cards, RAM and ROM memory, modem, hard disk drive memory, etc.). The automated microwave digestion system components shown, for example, in FIG. 2, are then initialized at step 306. The user is thus presented with a screen similar to that shown in FIG. 8, from which the user can input all of the parameters, such as the number of tubes to be processed, the cooking method to be utilized and any other parameter or protocol utilized in connection with the microwave digestion oven 102 capable of being programmed.

A determination is then made at step 308 of whether the operator has instructed the system to start processing. If a negative determination is made at step 308, then step 308 is repeated. If an affirmative determination is made at step 308, then a determination is made at step 310 of whether the operator has completed the digestion process which would necessarily require that the sample tubes 104 be loaded into the microwave digestion oven 102. If an affirmative determination is made at step 310, then the program jumps to step 400 and executes the load event subroutine.

The load event subroutine is shown in diagrammatic flowchart form in FIG. 4. Once the load event subroutine is called at step 400, the tube gripper 114 is caused to pick up the first or next tube condenser 112 for the specified sample number which is less than seven, at step 402. The gripper 114 then places the tube condenser 112 on the first or next sample tube 104 for the specified sample number less than seven, at step 404. Then, the gripper 114 moves the sample tube 104 having the tube condenser 112 just placed thereon to the first or next cavity 110 of the microwave digestion oven 102, all at step 406. After placing the sample and tube condensers combination in the appropriate microwave cell 110 of the microwave digestion oven 102, the gripper 114 is then caused to lower the appropriate reagent/exhaust arm 108, at step 408. Then, at step 410, the particular cavity 110 into which the sample and tube condenser combination was just placed is started. At step 412, the load event is ended and the program control returns to the main program.

If a negative determination is made at step 310 or after the end of an event at step 412, a determination is made at step 312 of whether an unload event has been requested. An unload event would be requested after the sample tube 104 has completed its indicated cooking time in the cavity 110 of the microwave digestion oven 102. If the appropriate time has elapsed, then an affirmative determination is made at step 312 and the supervisory program jumps to the unload event subroutine at step 500. When called at step 500, the unload event then washes the appropriate tube condenser 112 with de-ionized water while at the same time diluting the sample tube 104 with 85 mL of de-ionized water at step 502. The gripper 114 is then commanded to raise the reagent/exhaust arm 108 of the specified cavity 110, at step 504. The tube gripper 114 then moves the tube condenser 112 sitting on the sample tube 104 for which cooking has just been completed to the next sample tube 104 to be cooked, if applicable, or to move the washed tube condenser 112 to the digestion tube rack 106 or to the tube condenser rack, all at step 506.

Then, at step 508, the sample tube 104 which has been cooked is removed by the tube gripper 114 from the oven cavity 110 and taken to the cap station 116. Then, at step 510, the tube gripper 114 places a cap 126 on the sample tube 104. At step 512, the gripper jaws 900, 902, are used to move the capped sample tube to the tube rack 106. The unload event subroutine then ends at step 412 and returns to step 310.

In the event of a negative determination at step 312, a determination is then made at step 314 of whether all of the events, the data for which have been inputted into the program by the lab technician have been completed. If a positive determination is made at step 314, meaning that each of the sample tubes 104 has been processed, then the main program jumps to the shutdown event subroutine at step 600.

Once called at step 600, the shutdown event subroutine parks the gantry 118 at step 602 and leaves the reagent/exhaust arm exhaust pump on for a predetermined time period, at step 604. The shutdown event subroutine then writes a run log at step 606 and then ends at step 412. The run log may contain such information as the time and date, sample identification information, operator ID, oven method filename and system errors/status.

If a negative determination is made at step 314, then a determination is made at step 316 of whether any errors have occurred. If a determination is made at step 316 that an error has occurred, then the error event subroutine is called at step 700. Once called at step 700, the error event subroutine writes a run log at step 606 and then stops the microwave digestion oven 102 at step 702. Then, at step 704, the gantry 118 is stopped. Next, at step 706, the exhaust pump which exhausts the reagent/exhaust arms 108 is left on. An error message is then displayed at step 708 for viewing by the lab technician. The error event subroutine then returns to the status display, at step 710.

In the event of a negative determination at step 316 or after step 710, the supervisory program updates the status display at step 318 and then jumps to again execute steps 310–316.

Generally speaking, the following steps, although not specifically set forth in connection with the description of the software shown in FIGS. 3–7 are performed during the automated microwave digestion processing of the samples contained in the sample tubes 104 such that all of the organic material in those samples has been destroyed. First, the vacuum pump which exhausts the reagent/exhaust arms 108 is turned on, as is the microwave digestion oven 102. Then, the syringe contained as part of the microwave digestion oven 102 is primed with the appropriate reagents. The first sample tube 104, which is usually sitting in the digestion tube rack 106, is then moved to the first available cavity 110 in the microwave digestion oven 102. A tube condenser 112 is then placed on top of the sample tube 104 using the tube gripper 114. Again using the tube gripper 114, the reagent/exhaust arm 108 is lowered to the top of the tube condenser 112. The program for operating that cell 110 of the microwave digestion oven 102 is then begun.

The first step in that operating program is the addition of reagent, such as nitric acid, to the sample tube 104. The digestion of the sample follows, in accordance with preset data previously input into the computer 200 by a lab technician. That data, which includes such information as the method of operating the cell 110, the length of time of operation, the temperature of operation and the timing and quantity of adding acid or other reagent, has previously been obtained experimentally. The initial acid, as well as the additional acid and/or reagent is added to the sample tube 104 by means of the syringe line 109, as previously discussed. The foregoing steps are then repeated until all six cavities 110 of the microwave digestion oven 102 contain a sample tube 104 and are in the process of cooking or heating the sample contained in each sample tube 104.

Approximately 85 mL of de-ionized water is added to the sample tube 104 by means of the syringe line 113. The de-ionized water is added before the reagent/exhaust arm 108 is raised to rinse the tube condenser 112 with de-ionized water, by means of the syringe pump 204 and the syringe line 113. When digestion has been completed in the first sample being cooked, the gripper 114 is used to raise the reagent/exhaust arm 108.

The washed tube condenser 112 is then removed from the cooked sample tube 104 using the gripper 114 and is then placed by the gripper 114 on the next sample tube 104 to be processed. The digested sample tube 104 is then capped with a cap 126, by means of the gripper jaws 900, 902. Then, the next sample tube 104 for which digestion has been completed is treated in the same manner as discussed above, until all samples have been digested. After all of the samples to be digested have been cooked, the exhaust pump is left on for some time.

Figure 10A:
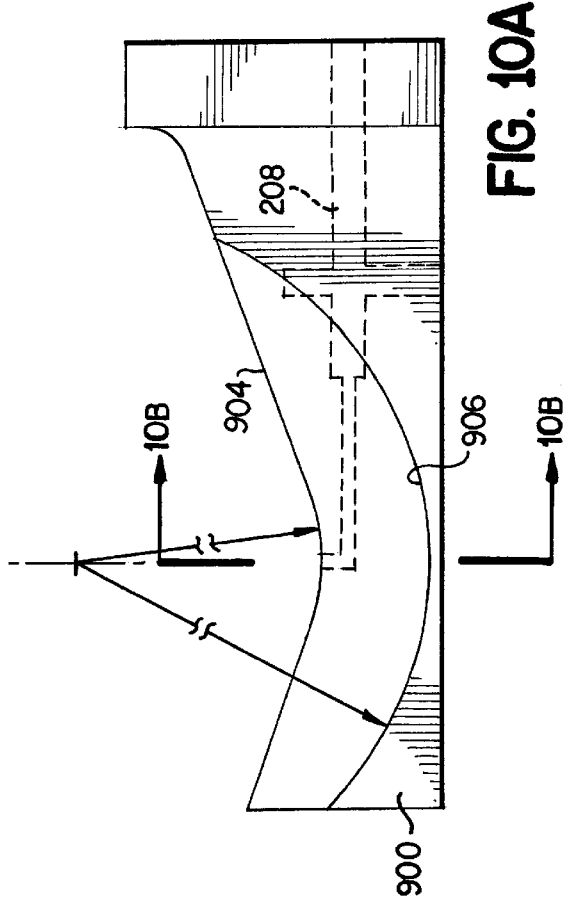
FIGS. 10A and 10B are perspective drawings showing the details of the gripper jaws of the tube gripper shown in FIG. 9.
Figure 10B:
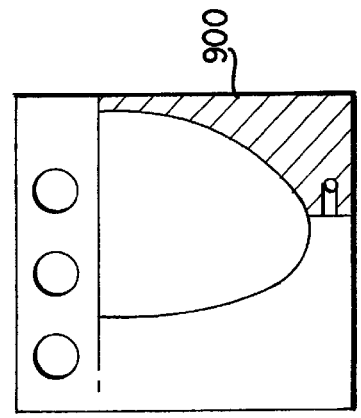

FIGS. 10A and 10B are perspective drawings which illustrate the curved radius shape developed for each of the gripper jaws 900, 902. For purposes of simplicity, only the right gripper jaw 900 is shown. The curved shape on the inside of the gripper jaw 900 shown in FIG. 10B is designed such that the top lip portion of the sample tube 104 and the bottom radiused portion of the tube condenser 112 are cradled in the two radii 904, 906 formed by the closed gripper jaws 900, 902.

As shown in FIGS. 9 and 10A, with the gripper jaws 900, 902 closed, the small radii 904 will form two sides of a circle slightly smaller than the diameter of the sample tube 104 to hold it in place. The same is true of the larger radii 906 and the tube condenser 112.

As previously discussed, each of the exhaust/reagent arms 112 has a lift disc 115 mounted to its top. The discs 115 have a radius smaller than the curved shape of the gripper jaw 900 shown in FIG. 10B. That allows the reagent/exhaust arms 108 being lifted using the disc 115 to rotate within the closed gripper jaws 900, 902 without binding.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. An automated microwave digestion system, comprising:
   a microwave digestion means for performing a digestion process on a sample;
   means for loading and unloading said samples to be digested by said microwave digestion means; and
   a digital data processor connected to both said microwave digestion means and means for loading and unloading said samples for controlling the operation of same such that a plurality of samples is automatically loaded into said microwave digestion means, digested and then unloaded, all under control of said digital data processor, wherein said means for loading and unloading said samples includes gripper means for moving containers holding said samples, and wherein said gripper means comprises opposed gripper jaws and such gripper jaws include detector means which produces two binary outputs, each indicative of a different light threshold between said gripper jaws.

2. The automated microwave digestion system of claim 1, wherein said two binary outputs provide information sufficient to detect at least three distinct states.

3. The automated microwave digestion system of claim 1, wherein said gripper jaws are specially shaped to conform to the configuration of containers holding said samples.

4. An automated microwave digestion system, comprising:
   a microwave digestion means for performing, a digestion process on a sample;
   means for loading and unloading said samples to be digested by said microwave digestion means; and
   a digital data processor connected to both said microwave digestion means and means for loading and unloading said samples for controlling the operation of same such that a plurality of samples is automatically loaded into said microwave digestion means, digested and then unloaded, all under control of said digital data processor, wherein said samples to be digested are held in containers and wherein condenser means are placed on top of said containers prior to digestion of said samples.

5. The automated microwave digestion system of claim 4, wherein said means for loading and unloading separates said condenser means from said container after said sample is digested.

6. The automated microwave digestion system of claim 4, further including means for washing said condenser means.

7. An automated sample digestion system, comprising:
   a digestion oven for digesting a plurality of samples, said digestion oven including means for adding at least one reagent to said sample during digestion;
   means for loading a plurality of containers holding said samples to be digested into said digestion oven and for positioning said means for adding at least one reagent with respect to said plurality of containers;
   said means for loading and also unloading said plurality of containers after each of said samples has been digested; and
   digital data processing means connected to said digestion oven and to said means for loading for controlling the operation of both said means such that a plurality of containers are loaded into said digestion ovens one at a time, the sample contained in said plurality of containers is digested and then each of said plurality of containers is unloaded from said digestion oven, wherein said means for loading and unloading said samples includes gripper means for moving containers holding said samples, a nd wherein said gripper means comprises opposed gripper jaws and such gripper jaws include detector means which produces two binary outputs, each indicative of a different light threshold between said gripper jaws.

8. The automated sample digestion system of claim 7, wherein said two binary outputs provide information sufficient to detect at least three distinct states.

9. The automated sample digestion system of claim 8, wherein said opposed gripper jaws are specially shaped to conform to the configuration of containers holding said samples.

10. An automated sample digestion system, comprising:
    a digestion oven for digesting a plurality of samples, said digestion oven including means for adding at least one reagent to said sample during, digestion;
    means for loading a plurality of containers holding said samples to be digested into said digestion oven and for positioning said means for adding at least one reagent with respect to said plurality of containers;
    said means for loading and also unloading said plurality of containers after each of said samples has been digested; and
    digital data processing means connected to said digestion oven and to said means for loading for controlling the operation of both said means such that a plurality of containers are loaded into said digestion ovens one at a time, the sample contained in said plurality of containers is digested and then each of said plurality of containers is unloaded from said digestion oven, wherein said samples to be digested are held in containers and wherein condenser means are placed on top of said containers prior to digestion of said samples.

11. The automated sample digestion system of claim 10, wherein said means for loading and unloading separates said condenser means from said container after said sample is digested.

12. The automated sample digestion system of claim 11, further including means for washing said condenser means.

13. A method for automatically digesting a plurality of samples, comprising the steps of:
    providing a microwave digestion means for performing a digestion process on said plurality of samples;
    providing means for loading and unloading said plurality samples to be digested by said microwave digestion means; and
    controlling the operation of said microwave digestion means and said means for loading and unloading using a digital data processor such that a plurality of samples is automatically loaded into said microwave digestion means, digested and then unloaded from said microwave digestion means, wherein said gripper means comprises opposed gripper jaws and such gripper jaws include detector means which produces two binary outputs, each indicative of a different light threshold between said gripper jaws.

14. The method of claim 13, wherein said two binary outputs provide information sufficient to detect at least three distinct states.

15. A method for automatically digesting a plurality of samples, comprising the steps of:

provided a microwave digestion means for performing a digestion process on said plurality of samples;

providing means for loading and unloading said plurality samples to be digested by said microwave digestion means; and controlling the operation of said microwave digestion means and said means for loading and unloading using a digital data processor such that a plurality of samples is automatically loaded into said microwave digestion means, digested and then unloaded from said microwave digestion means, wherein said samples to be digested are held in containers and wherein condenser means are placed on top of said containers prior to digestion of said samples.

16. The method of claim 15, wherein said means for loading and unloading separates said condenser means from said container after said sample is digested.

17. The method of claim 15, further including the step of washing said condenser means.

* * * * *